United States Patent [19]

van Riet

[11] Patent Number: Plant 7,486

[45] Date of Patent: Apr. 2, 1991

[54] LILY PLANT NAMED WHITE SHEEN

[76] Inventor: Joseph E. J. van Riet, Koewachtsteenweg 7, 9080 Moerbeke-Waas, Belgium

[21] Appl. No.: 489,342

[22] Filed: Feb. 28, 1990

[51] Int. Cl.[5] ..... A01h 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of lily plant named White Sheen, particularly characterized by its relatively short height; brilliant dark green leaves; vigorous healthy growth habit; regular and attractive inflorescence; large flower size; pure ivory white tepal color; large buds which are greenish-white in color; size 12–14 bulb produces five flowers; excellent lasting quality; and adaptibility to pot or cut stem culture, with reduced height making it particularly suitable for growing in pots.

1 Drawing Sheet

The present invention comprises a new and distinct cultivar of lily botanically known as Lilium (Longiflorum hybrid), and hereinafter referred to by the cultivar name White Sheen. The new variety is categorized commercially as a genetically short longiflorum hybrid, Division R.H.S. IX(d) in the Horticultural Classification of the Genus Lilium adopted by The Royal Horticultural Society of London, England.

White Sheen is a product of a planned breeding program which had the objective of creating new genetically short longiflorum cultivars. The breeding program was initiated in 1979 by the inventor Joseph E. J. van Riet in Moerbeke-Waas, Belgium.

White Sheen was originated by me from a hybridization made in the noted breeding program in Moerbeke-Waas, Belgium. The female parent was a seedling developed from the cross of the cultivars Ace × Nellie White. The male parent of White Sheen was the cultivar named White America.

White Sheen was discovered and selected by the inventor as one flowering plant within the progeny of the stated cross in 1980 in a controlled environment in Moerbeke-Waas, Belgium.

The first act of asexual reproduction of White Sheen was accomplished when scales were taken by the inventor in a controlled environment in Moerbeke-Waas, Belgium. Continued asexual reproduction by bulb scale and from bulblets has demonstrated that the combination of characteristics as herein disclosed for White Sheen are firmly fixed and are retained through successive generations of asexual reproduction.

White Sheen has not been observed under all possible environental conditions. The phenotype may vary significantly with variations in environment such as temperature, light intensity, and day length. The following observations, measurements, and comparisons describe plants grown in Moerbeke-Waas, Belgium under greenhouse conditions which approximate those generally used in commercial practice.

The following traits have been repeatedly observed and are determined to be basic characteristics of White Sheen which in combination distinguish this lily as a new and distinct cultivar.

1. Relatively short height.
2. Brilliant dark green leaves.
3. Vigorous, healthy growth habit.

4. Regular and attractive inflorescence.
5. Large flower size and pure ivory white tepal color.
6. Large buds which are greenish white in color.
7. A size 12–14 bulb gives five (5) flowers.
8. Excellent lasting quality both when pot grown or as cut stem.
9. Adaptability to pot or cut stem culture, with its reduced height making it particularly suitable for growing in pots.

The accompanying color photographic drawing comprises a perspective view of buds, typical flowers and foliage of White Sheen grown in an approximately 6 inch pot. The colors are as true as possible with illustration of this type. In the following description, color references are made to The Royal Horticultural Society Color Chart.

Plant:

*Form.*—Bulbous monocotyledon

*Height.*—Bulbs 12–14 cm (4.8–5.6″) in circumference produce stems about 35 cm (14″) tall when flowers are forced under glass; field grown bulbs produce stems about 25–30 cm (10–12″) tall in their second season after scaling.

*Growth.*—Very vigorous and strong.

Foliage:

*Arrangement.*—Leaves alternate.

*Size of leaves.*—Average length 16 cm (6.5″); average width 2 cm (1″).

*Shape of leaves.*—Elliptical, with acute tips.

*Texture of leaves.*—Leaves smooth and glossy on both upper and lower surfaces.

*Margin.*—Leaves entire (not serrated).

*Color.*—Brilliant dark green.

*Ribs and veins.*—Typical monocotyledonous venation; light green parallel veins.

*Stem.*—Green.

Inflorescence: Bulbs which are 12–14 cm (4.8–6″) in circumference produce 5 buds. Before blooming the buds become ivory white. The peduncle and pedicels are smooth and glossy.

Buds:

*Size.*—About 18 cm (6.5″) long; about 9 cm (3.25″) wide.

*Form.*—Large, white, typical of Longiflorum hybrid lilies.

*Opeining.*—Slowly, in about one hour in response to morning light. Flowers further up the stem open on subsequent days over an interval of 2–3 weeks.

*Color of mature buds.*—Ivory white and glossy.

The flowers:

*Blooming characteristics.*—Flowers in mid-season, late June and early July in the Netherlands, once, profusely; suited for year-round culture in pots.

*Flower size.*—Flower diameter is 15–18 cm (6–7.2").

*Inner tepals.*—6–7 cm wide (2.4–2.8").

*Outer tepals.*—5–6 cm wide (2–2.4").

*Shape when flower first opens.*—Completely gleaming white; the ends of the petals become more scrolly when the flower ages.

*Tepal arrangement.*—Typical of the genus Lilium, with 6 entire imbricated tepals.

*Color, outer petals.*—Tube, greenish white; petal transparent white with ivory-white midrib, 155D.

*Color, base of tepals.*—White with long green midrib in the throat, 144D.

*Color, inside tepals.*—Like the outer tapals.

*Color, reverse of tepal.*—The color of the reverse is also beautiful white.

*Spotting pattern.*—The flower has no spots.

*Tepal duration.*—Tepals remain on individual flower for about 10 days. When the stem has 5 flowers the tepals remain for about 21 days; tepals fall as flower ages.

*Flower texture.*—Good texture, not affected by high temperatures or wet conditions.

*Pedicel.*—Pedicel is sturdy and upright, ascending at 45° angle, except for upper one-third (⅓) which is at about 90°. Length: 4–5 cm (1.6–2"). Color: Green.

*Fragrance.*—Sweet.

*Lasting quality.*—Flowers remain on plants for about 14 days. Flowers remain on cut flower stem for about 10 days with adequate light.

Reproductive organs:

*Stamens and anthers.*—Typical of genus Lilium; six versatile anthers hang (singly) from 6 narrow filaments.

*Filaments.*—8—10 cm (3.2–4") long, 144D in color.

*Pollen.*—Lemon-yellow, 13A.

*Pistil.*—1, typical of genus Lilium; style is 9–11 cm (3.6–4.4") long.

*Stigma.*—Wide, yellow-green, 145D.

*Ovary.*—Typical of genus Lilium; superior, single 6 chambered.

The fruit Fertile, capsule is oblong with 6 chambers. Color at maturity is medium green to dark green, overlaid with soft yellow. Fades to soft brown when fruit splits open to release seeds.

The bulbs:

*Color.*—White.

*Size.*—Usual commercial size is 10–18 cm (4–7.2") in circumference; bulbs can be grown to a larger size if this is desired.

I claim:

1. A new cultivar of lily plant named White Sheen, as illustrated and described.

* * * * *

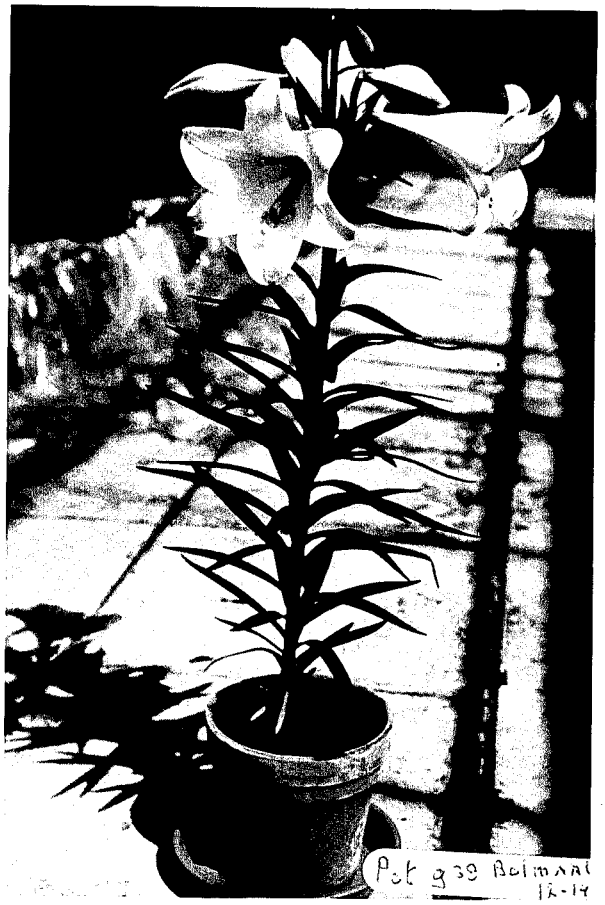
Pat g 39 Belmont
12-14